United States Patent [19]

Fischione

[11] Patent Number: 4,655,749
[45] Date of Patent: Apr. 7, 1987

[54] ANGIOPLASTY PRESSURE CONTROLLER

[76] Inventor: Eugene A. Fischione, 216 Red Oak Dr., Pittsburgh, Pa. 15239

[21] Appl. No.: 781,746

[22] Filed: Sep. 30, 1985

[51] Int. Cl.⁴ .................. A61M 5/315; A61M 29/02
[52] U.S. Cl. ..................................... 604/98; 604/184; 128/67; 128/344; 128/748; 92/51
[58] Field of Search ............... 604/97, 98, 99, 101, 604/15, 181, 184, 224, 226; 128/344, 673, 748, 658; 92/51, 52

[56] References Cited

U.S. PATENT DOCUMENTS

| | | | |
|---|---|---|---|
| 4,209,023 | 6/1980 | Layton | 128/748 |
| 4,244,366 | 1/1981 | Raines | 604/211 |
| 4,370,982 | 2/1983 | Reilly | 604/98 |
| 4,439,185 | 3/1984 | Lundquist | 604/99 |
| 4,464,171 | 8/1984 | Garwin | 604/164 |
| 4,526,175 | 7/1985 | Chin et al. | 604/98 |

FOREIGN PATENT DOCUMENTS 0115931 8/1984 European Pat. Off. ............ 604/184

Primary Examiner—Stephen C. Pellegrino
Assistant Examiner—John D. Ferros
Attorney, Agent, or Firm—Wegner & Bretschneider

[57] ABSTRACT

An angioplasty pressure controller having a housing with a slidable pressure cylinder in it. A drive screw is connected to a piston in the cylinder and arranged for fine adjustment by turning the drive screw. An engagement slide to provide a rapid means to create pressure or vacuum. A connecting rod is attached at one end to the cylinder and at the other end to the plunger of a syringe. A pressure gauge is connected to the inside chamber of the cylinder.

5 Claims, 12 Drawing Figures

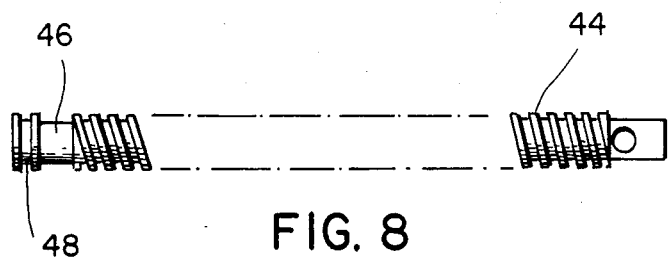
FIG. 8
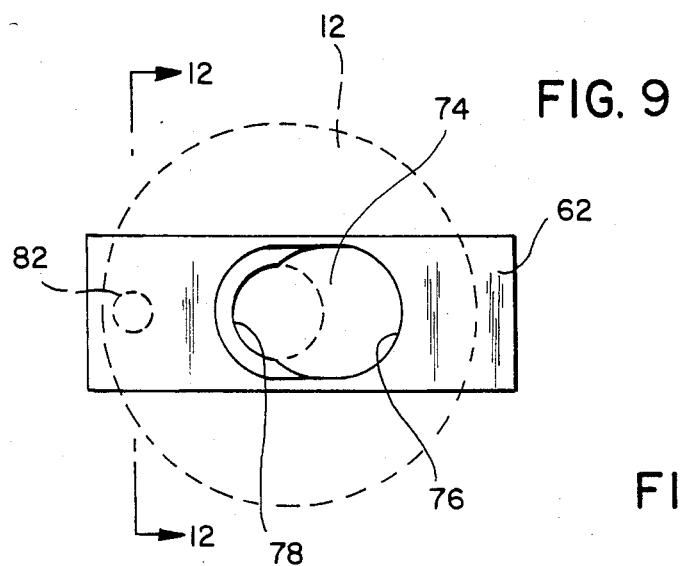
FIG. 9
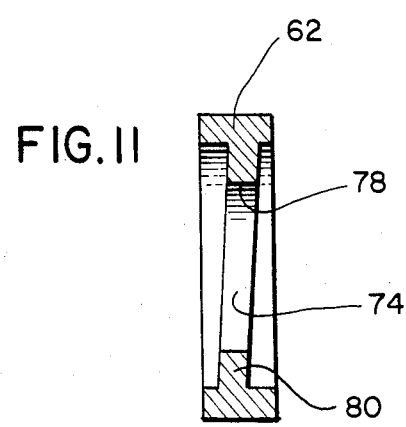
FIG. 11
FIG. 10
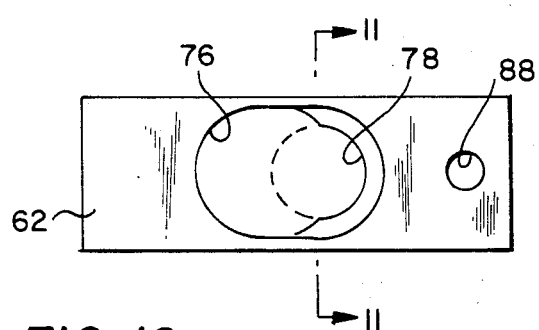
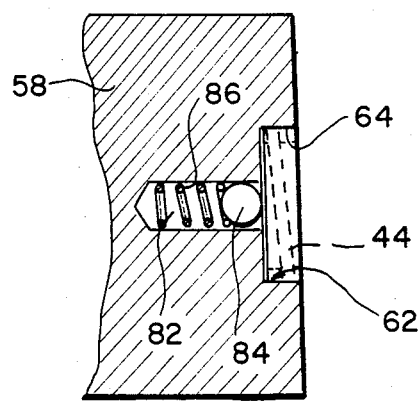
FIG. 12

ANGIOPLASTY PRESSURE CONTROLLER

BACKGROUND OF THE INVENTION

This invention relates to angioplasty and, more particularly, this invention relates to the control of the pressure in an angioplasty system.

Angioplasty is a procedure which is commonly used for dilating arteries which are occluded or blocked. Typically, a catheter is used which contains a balloon at the end which is inserted into the artery. The balloon is inflated by being filled and pressurized with a fluid from a standard syringe. The present invention is particularly concerned with a device for exerting and maintaining pressure on the syringe used to inflate the balloon catheter used in coronery angioplasty (dilatation) or peripheral angioplasty. In addition, the device is so designed to provide a vacuum resulting in the collapse of the balloon. Standard syringes of 5 cc and 10 cc volume are most commonly used to inflate the balloon catheter.

Typically, the force used to expand the balloon is exerted by hand, that is, by manually pushing the plunger of the syringe. While this force is being exerted, it is difficult to maintain constant pressure by hand. Hence, there has been a need for an apparatus to exert the force and maintain a constant pressure.

An extremely complex apparatus is disclosed in U.S. Pat. No. 4,202,346 in the name of Granier. This prior art apparatus is designed to selectively fill the catheter with different fluids for different purposes. The fluids are supplied by separate syringes and supply of the fluids from these syringes is governed by turning a micrometer screw connected to each syringe.

U.S. Pat. No. 4,370,982 issued to Riley discloses a device for controlling the pressure of fluid injected into an angioplasty catheter. This device has an outer cylindrical housing and an inner cylinder arranged in the housing to slide axially. An annular chamber is formed between the inner cylinder and the inner wall of the outer housing. A syringe is fixed to the inner cylinder. A pressure gauge communicates with the annular chamber. Thus, when pressure is applied to the plunger of the syringe to force fluid from the syringe into the catheter, the sliding inner cylinder is also caused to move axially, thereby secondarily, applying pressure to fluid in the annular chamber, this pressure being measured by the pressure gauge. Thus, the pressure shown on the gauge is, indirectly, a measure of the pressure applied to the syringe. In an alternate embodiment, a drive bolt engages a threaded bore which is to one side of, and parallel to, the syringe. A connecting lever connects the drive bolt with the plunger of the syringe.

The Riley device has a number of disadvantages, not the least of which is its complexity. The pressure is applied directly to the syringe which is fixed to the cylinder. Pressure is secondarily, therefore, applied to fluid in the annular chamber by causing the cylinder to slide within the housing. The drive bolt is connected by means of a linkage directly to the plunger of the syringe and this, also, does not provide the necessary positive pressure adjustment.

SUMMARY OF THE INVENTION

It is, therefore, a primary object of the present invention to provide an angioplasty pressure controller which is free of the aforementioned and other such disadvantages.

It is another object of the present invention to provide an angioplasty pressure controller which will exert and maintain pressure or vacuum in a constant manner.

It is a further object of the present invention to provide an angioplasty pressure controller which has very few moving parts and is easy and inexpensive to manufacture.

It is yet another object of the present invention to provide an angioplasty pressure controller having a gauge which accurately indicates the pressure exerted in the catheter without the fear of contamination of the catheter.

Consistent with the foregoing objects, the angioplasty pressure controller of the present invention comprises a hollow elongated housing to one end of which a syringe barrel is fixed; a pressure cylinder slidingly disposed in the housing, a piston disposed in the cylinder and, together with the cylinder, defining a pressure chamber filled with a fluid, and a pressure gauge mounted on the cylinder but extending out of the housing and operatively communicating with the chamber; a connecting rod fixed to one end of the cylinder and extending out of the first end of the housing into the syringe barrel affixed to a plunger which serves as a receptacle for a syringe plunger tip; and a drive screw fixed to the piston and threadedly engaging the other end of the housing by means of an engagement slide. When the drive screw is turned to apply pressure to the piston, the piston, in turn, applies pressure to the fluid in the chamber and the pressure of the fluid is read by the gauge. At the same time, the pressure cylinder is caused to slide axially in the housing in an amount determined by the pitch of the screw and the number of turns applied to the screw. When the cylinder slides in the housing, the connecting rod which is fixed to the cylinder is also caused to move axially, thereby moving the syringe plunger tip and applying pressure to the fluid in the syringe. When it is so desired to collapse the balloon for the purpose of introducing the balloon into the artery or to evaluate the effects of the angioplasty with the balloon at the occluded or blocked area, the syringe plunger tip is retracted and the resulting vacuum evacuates the fluid from the balloon thus collapsing the balloon. By activating the engagement slide and preventing forward axial motion of the syringe plunger tip, the balloon is maintained in the collapsed state.

BRIEF DESCRIPTION OF THE DRAWINGS

The invention will be better understood, and objects other than those set forth above will become apparent, when consideration is given to the following detailed description thereof. Such description makes reference to the annexed drawings wherein:

FIG. 8 is an elevational view of the drive screw;

FIG. 9 is a plan view of the engagement slide used as locking means showing its relationship with the housing;

FIG. 10 is a plan view of the engagement slide, from the other side, alone;

FIG. 11 is a cross-sectional view taken along the line 11—11 of FIG. 10; and

FIG. 12 is an enlarged cross-sectional view taken along the lines 12—12 of FIG. 9.

DESCRIPTION OF THE PREFERRED EMBODIMENTS

Figure 1:
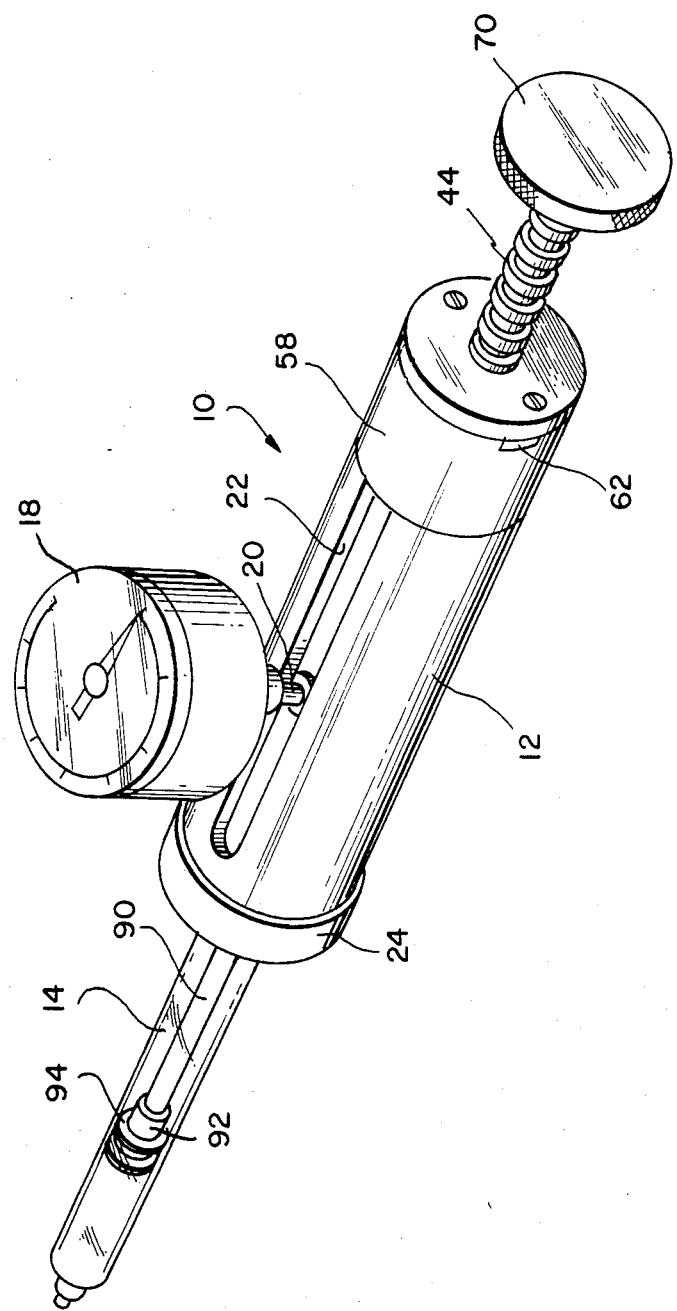
FIG. 1 is a perspective view of the angioplasty pressure controller according to the instant invention, with a conventional syringe shown as being attached thereto.
Figure 2:
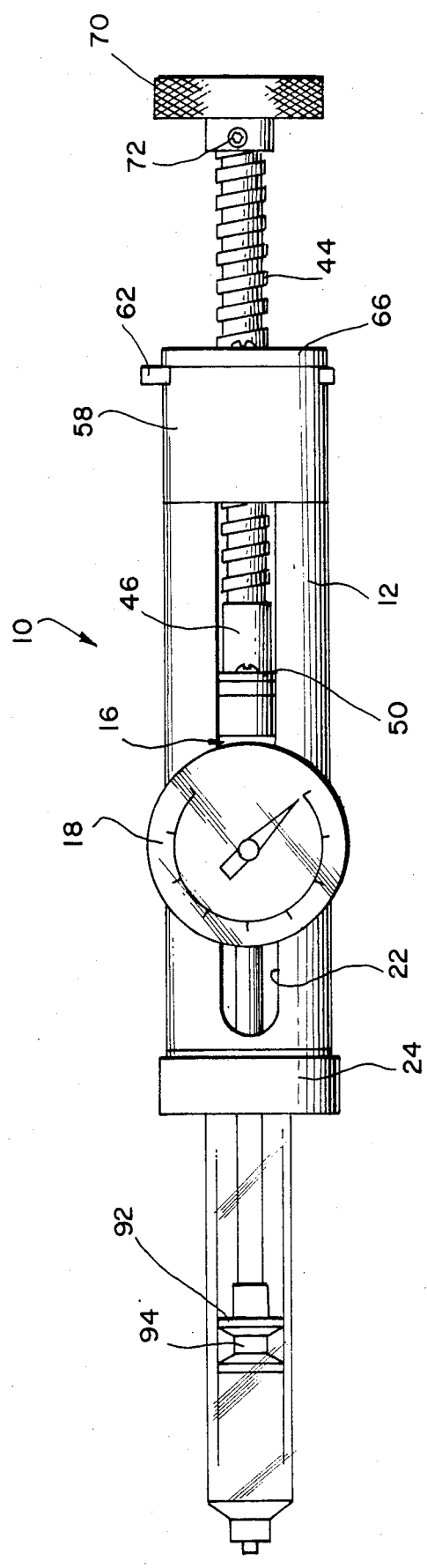
FIG. 2 is a top plan view of the angioplasty pressure controller of FIG. 1.

Referring first to FIGS. 1 and 2, the angioplasty pressure controller 10 of the instant invention comprises a housing 12 which is preferably cylindrical and is adapted to have affixed at one end thereof a standard syringe 14. The means for mounting the syringe will be described in more detail hereinbelow. Slidingly disposed within housing 12 is pressure cylinder assembly 16. Pressure cylinder assembly 16 comprises pressure gauge 18 fixed to pressure cylinder 30 through a suitable fitting 20 which protrudes through an elongated opening 22 in housing 12.

Figure 3:
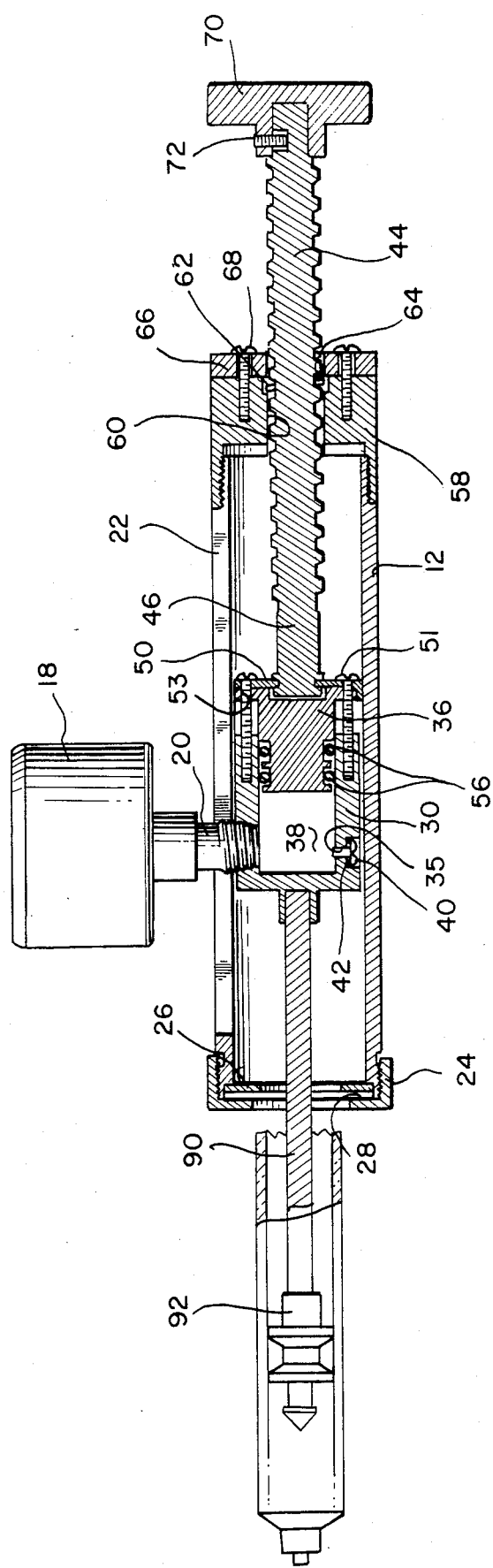
FIG. 3 is an elevational view, in cross-section of the angioplasty pressure controller.
Figure 4:
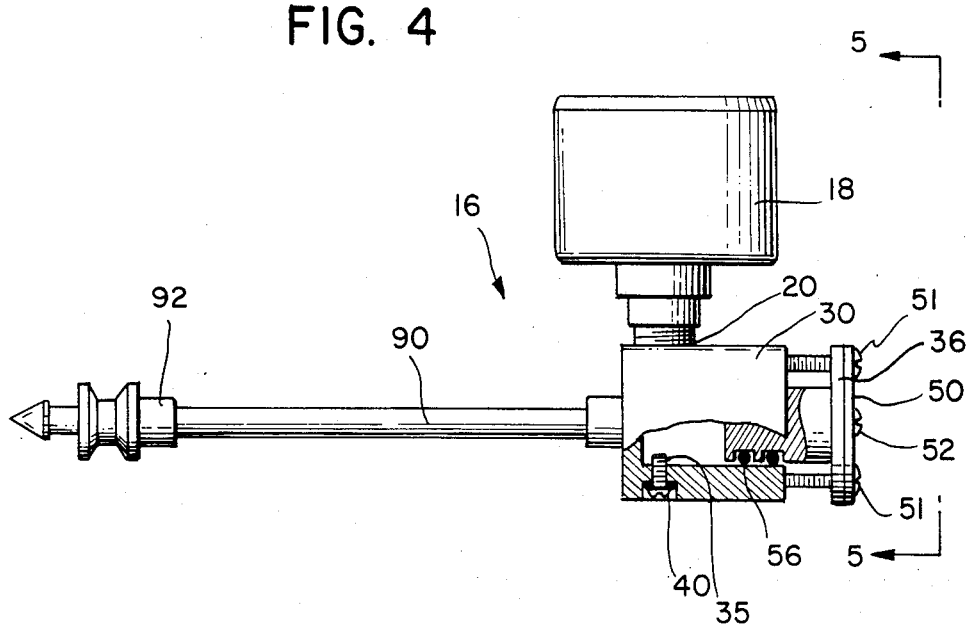
FIG. 4 is an elevational view of the pressure cylinder and plunger assembly, partly in cross-section for illustrative clarity.

Attention is now directed to FIG. 3 wherein, in conjunction with FIG. 1 it will be seen that the syringe 14 is affixed to housing 12 by unscrewing syringe retaining screw cap 24. The syringe is placed with its flange against syringe backup washer 26 and syringe retaining screw cap 24 is then screwed back onto housing 12. Thus, the syringe flange is sandwiched in the space 28 between syringe retaining screw cap 24 and syringe back-up washer 26. An assembly generally designated by the numeral 16 (FIG. 4) comprises gauge 18, pressure cylinder 30, piston 36, connecting rod 90, and associated elements. Pressure cylinder 30 is slidingly disposed within housing 12 and pressure gauge 18 is fixed to pressure cylinder 30 by means of a standard screw-type fitting 20 which extends through the elongated opening 22 in the housing 12.

Figure 6:
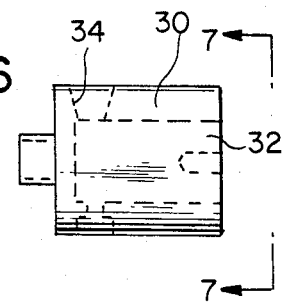
FIG. 6 is an elevational view of the pressure cylinder alone.
Figure 7:
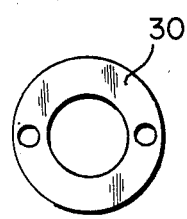
FIG. 7 is an end view thereof.

Pressure cylinder 30, as shown in FIGS. 6 and 7, is preferably cylindrical, having a blind hole 32 and a threaded hole 34 communicating therewith. Threaded hole 34 is for receiving the fitting 20.

Piston 36 is disposed in pressure cylinder 30, thereby forming a chamber 38 which is filled with fluid. A hole 35 is provided communicating the chamber 38 with the outside for purposes of adding fluid, bleeding air bubbles, and the like from the chamber. This hole is ordinarily sealed with screw 40 and O-ring 42.

Figure 5:
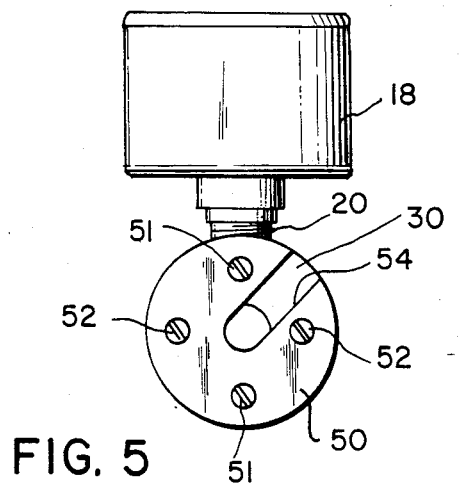
FIG. 5 is an end view thereof.

Drive screw 44, as seen in FIG. 8, is an elongated drive screw, preferably with square threads, having an unthreaded portion 46 at one end terminating in a pair of spaced-apart flanges defining a locking groove 48. End portion 46 of drive screw 44 abuts against piston 36 and is fixed in place by drive screw retaining plate 50 which, in turn, is fixed to piston 36 by means such as screws 52. Drive screw retaining plate 50 is slotted as shown at 54 (FIG. 5) to engage locking groove 48. Guide screws 51 fitting through clearance holes 53 in the piston 36 and drive screw retaining plate 50 provide a means to prevent rotation of the piston 36 in the cylinder 30 and to retract the slidingly disposed cylinder assembly 16 when outward axial movement of the syringe plunger tip 94 to rapidly decrease pressure or to create vacuum is required. O-rings 56 are provided to seal the cylinder 30 and piston 36, preventing leakage from chamber 38.

Drive cap 58 is threadedly attached to housing 12 and drive screw 44 passes through a bore 60 therethrough. Engagement slide 62 is slidingly disposed in a slot 64 which is slightly wider than the diameter of bore 60 and of sufficient width to accommodate engagement slide 62 without binding and end plate drive cap 66 is affixed thereover by means of screws 68 or the like to hold engagement slide 62 in place. Knob 70 is affixed to the end of drive screw 44 by suitable means such as a set screw 72.

Referring to FIGS. 9–12, it will be seen that engagement slide 62 has an opening which has a larger diameter portion 76 and a smaller diameter portion 78. The wall surrounding the smaller diameter portion 78 is tapered in a manner shown in FIG. 11. Thus, while the opening 74 is axial, the wall 80 surrounding the opening is slanted when seen in cross-section. The angle of slant is preferably approximately equal to the pitch of the threads of drive screw 44.

A blind hole 82 is provided in drive cap 58 and a detent ball 84 is provided therein biased outwardly by spring 86 to abut engagement slide 62. When ball 84 engages hole 88 in engagement slide 62, the slide is locked in place, with the smaller diameter part of the opening 78 engaging the threads of drive screw 44 whereby the drive screw 44 can be turned in either direction to apply pressure, or release pressure or maintain vacuum, as desired by the user. When the drive screw is to be moved inwardly or outwardly for gross adjustment, or release of pressure or vacuum, engagement slide 62 is moved out of engagement with ball 84 to the extent where the larger diameter portion of the hole 76 surrounds drive screw 44.

Connecting rod 90 is fixed to the closed end of cylinder 30. A standard syringe plunger tip 94 is affixed to the plunger 92 which in turn is permanently attached by means of soldering or the like to the connecting rod 90.

Thus, it will be seen that the pressure controller of the present invention is completely self-contained and cannot contaminate the syringe. Application and adjustment of the pressure in the syringe is easily made merely by turning knob 70 to screw drive screw 44, in engagement with engagement slide 62, inwardly. The result of this is two-fold. First, pressure cylinder 30 is caused to slide axially in housing 12, thereby causing connecting rod 90 and syringe plunger tip 94 to move axially in syringe 14 while syringe 14 is held in place by syringe retaining screw cap 24. At the same time, pressure is applied to fluid in chamber 38 and a direct readout of this pressure is seen on gauge 18. Application of vacuum in the syringe is made by merely moving the engagement slide 62 until the open portion 76 surrounds the drive screw 44 and pulling axially outward on the knob 70, resulting in the retracting motion of the piston 36 disposed in the cylinder 30. The retracting motion continues until the drive screw retaining plate 50 contacts the head of the guide screws 51. Through the connection of the guide screws 51 to the pressure cylinder 30, additional retracting axial motion results in the retraction of the pressure cylinder assembly 16 and therefore the syringe plunger tip 94 in the syringe 14. Once a sufficient amount of vacuum, as determined by the user has been achieved, position the engagement slide 62 such that the smaller diameter part of the opening 78 engages the threads of the drive screw 44 thus maintaining vacuum.

It should be apparent that the objects set forth at the outset to this specification have been successfully achieved. Moreover, while there is shown and described present preferred embodiments of the invention, it is to be distinctly understood that the invention is not limited thereto, but may be otherwise variously embodied and practiced within the scope of the following claims.

What is claimed is:

1. An angioplasty pressure controller comprising:
   (A) a hollow elongated housing adapted to fixedly receive a syringe barrel at one end thereof;
   (B) a pressure cylinder slidingly disposed in said housing, a piston disposed in said cylinder, said cylinder and piston defining a pressure chamber filled with a fluid, and a pressure gauge mounted on said cylinder to extend out of said housing and operatively communicating with said chamber;
   (C) a connecting rod fixed, at one end, to one end of said cylinder and extending out of said one end of said housing into said syringe barrel to be affixed to a syringe plunger tip;
   (D) a drive screw fixed at one end to said cylinder piston extending through the other end of said housing and mounted for rotational and axial movement therein.

2. A device as claimed in claim 1, wherein said housing is cylindrical.

3. A device as claimed in claim 2, further comprising locking means which comprises a plate slidingly mounted at said other end of said housing transversely thereof and having an opening therein, one end of said opening being at least as large as the outer diameter of said drive screw and the other end of said opening being smaller than said outer diameter but at least as large as the diameter of said drive screw between the threads thereof.

4. A device as claimed in claim 3, wherein said opening is bounded by an area of reduced thickness, said area being pitched at an angle approximately equal to the pitch of said screw.

5. A device as claimed in claim 4, further comprising a detent ball mounted in said housing and normally biased to bear against said plate.

* * * * *